United States Patent [19]

Sircar et al.

[11] Patent Number: 4,602,019

[45] Date of Patent: Jul. 22, 1986

[54] INDENO[1,2-C]PYRIDAZIN-3-ONE DERIVATIVES USEFUL AS CARDIOTONIC AND ANTIHYPERTENSIVE AGENTS

[75] Inventors: Ila Sircar; James A. Bristol, both of Ann Arbor, Mich.

[73] Assignee: Warner-Lambert Company, Morris Plains, N.J.

[21] Appl. No.: 575,412

[22] Filed: Feb. 2, 1984

Related U.S. Application Data

[63] Continuation-in-part of Ser. No. 487,780, Apr. 22, 1983, abandoned.

[51] Int. Cl.[4] .................... C07D 403/04; A61K 31/50
[52] U.S. Cl. .................................. 514/248; 544/234; 544/115; 544/60; 260/243.3
[58] Field of Search ........................ 544/234; 514/248

[56] References Cited

U.S. PATENT DOCUMENTS 3,464,988  9/1969  Holava et al. ...................... 544/234
4,355,164  10/1982  Youssefyeh ........................ 544/234

OTHER PUBLICATIONS

Cignarella, et al., Chem. Abstracts, vol. 90, entry 72131z, (1979).
Curran, et al., J. Med. Chem., vol. 17, No. 3, (1974), pp. 273-281.
Holava, et al., J. Med. Chem., vol. 14, No. 3, (1971), pp. 262-264.

*Primary Examiner*—Donald G. Daus
*Assistant Examiner*—William A. Teoli, Jr.
*Attorney, Agent, or Firm*—Jerry F. Janssen

[57]  ABSTRACT

Substituted 2,5-dihydro- and 2,4,4a,5-tetrahydro-3H-indeno[1,2-c]pyridazin-3-ones and pharmaceutically acceptable salts thereof are useful as cardiotonic and antihypertensive agents.

13 Claims, No Drawings

INDENO[1,2-C]PYRIDAZIN-3-ONE DERIVATIVES USEFUL AS CARDIOTONIC AND ANTIHYPERTENSIVE AGENTS

CROSS-REFERENCE TO RELATED APPLICATIONS

This application is a continuation-in-part of application Ser. No. 487,780 filed Apr. 22, 1983, now abandoned.

BACKGROUND OF THE INVENTION

Halo-indeno-pyridazinones, particularly 7-fluoro-3H-indeno[1,2-c]pyridazin-3-one, have been described as having antiinflammatory activity in *Il Farmaco, Ed. Sci.* 37 (2):133–40 (1981).

The present invention relates to substituted-3H-indeno[1,2-c]pyridazin-3-ones cardiotonic and antihypertensive agents.

SUMMARY OF THE INVENTION

The present invention relates to novel substituted-3H-indeno[1,2-c]-pyridazin-3-ones useful as cardiotonic and antihypertensive agents having the structural formula (I):

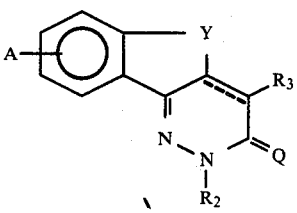

wherein represents a double or single bond between two carbon atoms; Y is

CO, O or S, in which m is 1 or 2 and $R_o$ is H or lower alkyl; $R_2$ is hydrogen or lower alkyl; Q is oxygen or sulfur, $R_3$ is hydrogen or lower alkyl; and A is any of the groups from a through e, and is attached to the 3- or 4-position of the phenyl ring:

a. 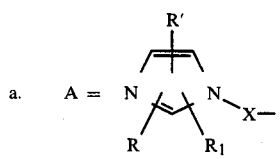

wherein $R_1$, $R'$, and $R$ are independently hydrogen or lower alkyl, $CH_2OH$, $SCH_3$, $SOCH_3$, $SO_2CH_3$, hydroxyalkyl, halogen, $(CH_2)_k NR''R'''$, wherein k is zero to two and $R''$ and $R'''$ are independently hydrogen or lower alkyl, wherein lower alkyl contains one to six carbon atoms; or, when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkyloxy, and (iii) pyridine ring; X is a bond, $(CH_2)_n$ or $O(CH_2)_{n+1}$ wherein n is one to four;

b. 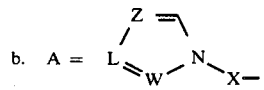

wherein
(i) $W=L=Z=CH$
(ii) $W=Z=N$ and $L=CH$ or
(iii) $L=Z=N$ and $W=CH$.
and X is the same as defined in 1a;

c. A=(i)

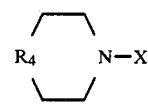

where $R_4$ is O, S, $NR_5$ wherein $R_5$ is hydrogen, alkyl, $COR_6$ where $R_6$ is a benzene ring optionally substituted by halogen, lower alkyl, hydroxy, lower alkoxy, and $CF_3$, or $(CH_2)_n R_6$ where n is zero to four and $R_6$ is the same as defined above; or (ii)

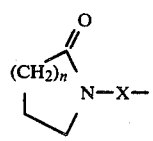

wherein n is one to three; or (iii)

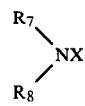

wherein $R_7$ and $R_8$ are lower alkyl or taken together form a five or six membered ring such as

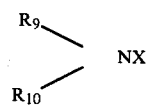

wherein $R_9$ and $R_{10}$ are independently hydrogen, lower alkyl, aryl, aralkyl, $CF_3$, hydroxy, lower alkoxy, $NHR_{11}$, wherein $R_{11}$ is hydrogen, lower alkyl or lower alkanoyl, or taken together are carbonyl or ethylenedioxy and the pharmaceutically acceptable salts thereof; X is the same as defined in 1a;

d. 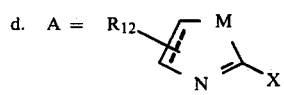

wherein represents a double or single bond between two carbon atoms; $R_{12}$ is hydrogen or lower alkyl; M is NH, O, or S, and X is either a direct bond or NH; or

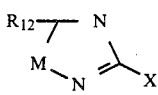

wherein X, M, and $R_{12}$ are the same as defined above, or e. $NHPR_{13}R_{14}$ wherein P is a bond or carbonyl; $R_{13}$ is lower alkyl, straight or branched; $R_{14}$ is hydrogen or lower alkyl, halo, $NR_{15}R_{16}$ wherein $R_{15}$ and $R_{16}$ are individually hydrogen, lower alkyl straight or branched or taken together to form a 5-, 6-, or 7-membered ring or a group as defined in 1a–1c; or $S(O)_nR_{17}$ where n is zero to two and $R_{17}$ is lower alkyl straight or branched, phenyl, and the pharmaceutically acceptance salts thereof.

DETAILED DESCRIPTION

The compounds of formula I where $R_2$ is hydrogen may exist in tautomeric forms, for example, as 3-(2H)-pyridazinones and/or 3-pyridazinols of formula IA, illustrated as follows.

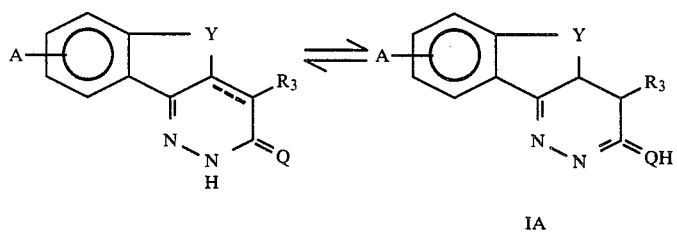

IA

The present invention also relates to 2,4,4a,5-tetrahydro-7-(substituted)-3H-indeno[1,2-c]pyridazin-3-ones having the structural formula II.

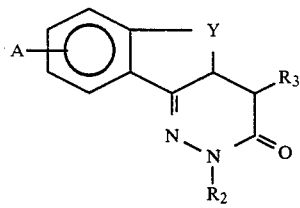

II wherein A, Y, $R_2$, and $R_3$ are the same as defined above and pharmaceutically acceptable salts thereof.

Another aspect of the present invention is a compound of the formula

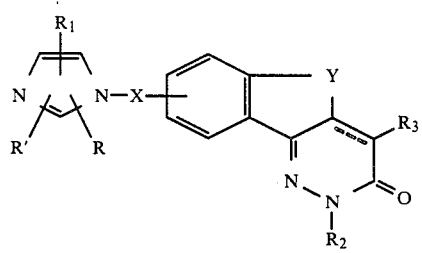

III wherein $R_1$, R', R, X, $R_2$, Y and $R_3$ are as defined above and pharmaceutically acceptable salts thereof.

Another aspect of the invention is a compound of the formula

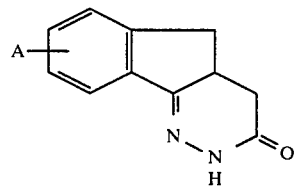

IV wherein A is as defined in sections (a) and (e) above. Preferable groups for A are imidazole or imidazole substituted by lower alkyl, S-lower alkyl, or $CH_2OH$; tetrahydrobenzimidazole, benzimidazole, or 1,2,4-triazole. When A is as defined in (d) above, the heterocyclic ring is preferably 2-thiazoline.

Particular aspects of the invention are the following compounds:
2,4,4a,5-tetrahydro-7-(1H-imidazol-1-yl)-3H-indeno[1,2-c]pyridazin-3-one; 2,4,4a,5-tetrahydro-7-(1-piperidinyl)-3H-indeno[1,2-c]-pyridazine-3-one; 2,4,4a,5-tetrahydro-7-(4-hydroxy-1-piperidinyl)-3H-indeno-[1,2-c]pyridazine-3-one; 2,4,4a,5-tetrahydro-7-(1,4-dioxa-8-azaspiro[4,5]dec-8-yl)-3H-indeno[1,2-c]pyridazin-3-one, and 2,5-dihydro-7-(1H-imidazol-1-yl)-3H-indeno[1,2-c]pyridazin-3-one.

Another aspect of the present invention relates to a cardiotonic composition for increasing cardiac contractility and/or an antihypertensive composition for lowering blood pressure, said composition comprising an effective amount of a compound of formula I and a pharmaceutically acceptable carrier.

The present invention further relates to the method for increasing cardiac contractility and/or lowering blood pressure in a patient requiring such treatment which comprises administering orally or parenterally in a solid or liquid dosage form to such patient an effective amount of a compound of the formula I and a pharmaceutically acceptable salt thereof together with a pharmaceutical carrier.

The process for producing the indeno[1,2-c]pyridazin-3-ones of the formula I comprises reacting a suitably substituted 2,3-dihydro-5-(substituted)-1-oxo-1H-2-acetic acid of the formula

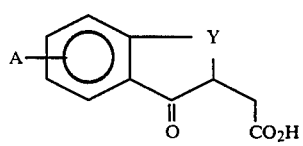

V with an $R_2$—$NHNH_2$ to give a compound of the formula I wherein represents a single bond and, if desired, dehydrogenating said product to a compound of the formula I wherein — represents a double bond. Known dehydrogenation procedures may be used such as bromination-dehydrobromination; noble metal catalyzed dehydrogenation such as palladium-catalyzed dehydrogenation, or oxidation-reduction procedures using $MnO_2$ or m-nitrobenzenesulfonic acid as the reagent according to the procedure set forth by W. V. Curran and A. Ross, *J. Med. Chem.*, 17, 273 (1974).

The compounds of the formula I where Q is sulfur may be conveniently prepared from the corresponding compounds of the formula I where Q is oxygen by treatment with phosphorus pentasulfide.

The starting materials of the formula V may be prepared by displacing the fluorine atom on the compound of the formula

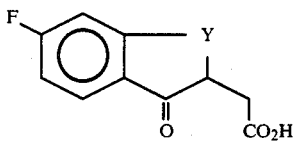

VI wherein Y is as defined above, with a compound corresponding to the group A as defined above in (a) through (e).

The displacement reaction is carried out at the boiling point of the solvent used, for example, pyridine, in the presence of an anhydrous salt, such as sodium or potassium carbonate, and also in the presence of a catalyst such as cuprous oxide.

In the case where A is as defined in (d) and X is a direct bond, the A group according to (d) may be prepared according to well-known steps from the corresponding cyano compounds; the fluorine atom on the compound of the formula VI is first displaced with a cyano group by reacting with potassium cyanide.

The compound of formula VI is known and is described in *Il Farmaco, Ed. Sci.* 37(2):133–40 (1981).

The compounds of formula (I) are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate, and the like, respectively. The compounds of formula I can also form salts with acetic acid, propionic acid, oxalic acid, malonic acid, glycolic acid, maleic acid, and fumaric acid.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The term "lower" in reference to alkyl and alkoxy means a straight or branched hydrocarbon chain of one to six carbon atoms such as, for example, methyl, ethyl, propyl, isopropyl, and the like. The term "halogen" includes fluorine, chlorine, bromine, and iodine but preferably is fluorine or chlorine.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

TEST FOR IN VIVO MYOCARDIAL INTROPIC ACTIVITY IN ANESTHETIZED DOG

This screen consists of determining the effects of increasing intravenous doses of compound on mycardial contractility (dP/dt max of left ventricular blood pressure), heart rate, and aortic blood pressure of the pentobarbital-anesthetized dog.

METHODS

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention, for example, 2,4,4a,5-tetrahydro-7-(1H-imidazol-1-yl)-3H-indeno[1,2-c]pyridazin-3-one, when administered intravenously at about 0.01 to 0.31 mg/kg cause dose related significant increases in cardiac contractility cardiac contractility with only low or minimal changes in heart rate and a moderate reduction in blood pressure. Accordingly, the compounds of the present invention are also useful as antihypertensive agents.

The following Example will further illustrate the invention without, however, limiting it thereto.

EXAMPLE 1

2,3-Dihydro-5-(1H-imidazol-1-yl)-1-oxo-1H-indene-2-acetic acid

A mixture of 3.3 g of 5-fluoro-2,3-dihydro-1-oxo-1H-indene-2-acetic acid [prepared by following the procedure of G. Cignarella, M. Loriga, G. A. Pinna, M. A. Pirisi, P. Schaitti, and D. Selva, Il Farmaco, Ed. Sci. 37(2), 133–40 (1981)], 2.2 g of anhydrous $K_2CO_3$, 1.65 g of imidazole, and 0.15 g of CuO in 15 ml of pyridine is heated to reflux for 24 hours. The reaction mixture is filtered, the filtrate is diluted with water, and the pH of the solution is adjusted to 5. The solid is filtered, washed with water, and crystallized from ethanol to yield 1.6 g of the product, 2,3-dihydro-5-(1H-imidazol-1-yl)-1-oxo-1H-indene-2 acetic acid, mp 224°–226° dec.

2,4,4a,5-Tetrahydro-7-(1H-imidazol-1-yl)-3H-indeno[1,2-c]pyridazin-3-one

A solution of 1.48 g of 2,3-dihydro-5-(1H-imidazol-1-yl)-1-oxo-1H-indene-2-acetic acid and 0.38 g of 85% hydrazine hydrate in 15 ml of ethanol is heated to reflux for three hours. The reaction mixture is filtered, the residue is washed with ethanol and purified by crystallization from ethanol to give 0.7 g of the product, 2,4,4a,5-tetrahydro-7-(1H-imidazol-1-yl)-3H-indeno[1,2-c]pyridazin-3-one, mp 263°–264° dec.

Anal. Calcd. for $C_{14}H_{12}N_4O$: C, 66.65; H, 4.69; N, 22.21; Found: C, 66.40; H, 4.93; N, 22.25.

EXAMPLE 2

2,4,4a,5-Tetrahydro-7-(1-piperidinyl)-3H-indeno[1,2-c]pyridazin-3-one (2a).

A mixture of 2 g of 5-fluoro-2,3-dihydro-1-oxo-1H-indeno-2-acetic acid, 2.65 g of $K_2CO_3$ and 50 ml of piperidine is heated to reflux for 20 hours. The suspension is then filtered over celite and the celite bed washed with methanol (50 ml). The combined filtrates are evaporated under reduced pressure to provide an oil. This crude oil is treated with aqueous hydrochloric acid (50 ml) and extracted with ethyl acetate (50 ml). The aqueous layer is separated, filtered and brought to pH 7 with ammonium hydroxide. This mixture is then extracted with 100 ml of $CHCl_3$:iPrOH (3:2). The organic layer is separated, washed with brine (100 ml), dried ($Na_2SO_4$) and evaporated to provide 1.4 g of an oil. This is dissolved in 25 ml of ethanol, 0.4 g of hydrazine hydrate added and the mixture is heated to reflux for two hours. The reaction mixture is cooled and filtered to provide 0.7 g of mp 282°–284° C.

Anal. Calcd. for $C_{16}H_{19}N_3O$: C, 71.35; H, 7.11; N, 15.60; Found: C, 71.38; H, 6.90, N, 15.56.

By following the procedure of Example 2 the following compounds were prepared:
(2b) 2,4,4a,5-tetrahydro-7-(3-hydroxy-1-piperidinyl)-3H-indeno[1,2-c]pyridazin-3-one, mp 246°–248°;
(2c) 2,4,4a,5-tetrahydro-7-(1,4-dioxa-8-azaspiro[4,5]dec-8-yl)-3H-indeno[1,2-c]pyridazin-3-one, mp 252°–254° C.

EXAMPLE 3

2,5-Dihydro-7-(1H-imidazo-1-yl)-3H-indeno[1,2-c]pyridazin-3-one

A solution of Bromine (0.6 g) in acetic acid (7 ml) is added dropwise to a stirred solution of the above dihydropyridazinone (0.8 g) in acetic acid (25 ml) at 95°–100° C. The reaction mixture is then heated at 110°–115° C. for six hours. After cooling the solid is filtered, washed with ether, and air-dried. This is suspended in 20 ml of water, pH of the solution is adjusted to 10. The solid is filtered, washed with water, and purified by chromatography over silica gel to give 0.23 g of the product, mp 304°–307° C.(d).

The compounds of Examples 4–13 were prepared by using the preparative method of Example 1 by reacting 5-fluoro-2,3-dihydro-1-oxo-1H-indene-2-acetic acid with the appropriate amine substrate in each case. With the exception of Example 9, the amine substrate compounds were obtained from commercial sources. The amine substrate of Example 9, tetrahydrobenzamidazole, was prepared by the method detailed in H. Schubert and and H. Fritsche, *J. Prakt. Chemie*, 4:207 (1958).

EXAMPLE 4

2,4,4a,5-Tetrahydro-7-(2-methyl-1H-imidazol-1-yl)-3H-indeno[1,2-c]pyridazin-3-one, mp 261°–264° C. (dec.).

EXAMPLE 5

2,4,4a,5-Tetrahydro-7-(2-ethyl-4-methyl-1H-imidazol-1-yl)-3H-indeno[1,2-c]pyridazin-3-one, mp 239°–241° C.

EXAMPLE 6

2,4,4a,5-Tetrahydro-7-(4-methyl-1H-imidazol-1-yl)-3H-indeno[1,2-c]pyridazin-3-one, mp 252°–253° C. (dec.).

EXAMPLE 7

2,4,4a,5-Tetrahydro-7-(4-hydroxymethyl-1H-imidazol-1-yl)-3H-indeno[1,2-c]pyridazin-3-one, mp 274°–277° C. (dec.).

EXAMPLE 8

2,4,4a,5-Tetrahydro-7-(4-phenyl-1H-imidazol-1-yl)-3H-indeno[1,2-c]pyridazin-3-one, mp 301°–302° C. (dec.).

EXAMPLE 9

2,4,4a,5-Tetrahydro-7-(4,5,6,7-tetrahydro-1H-benzimidazol-1-yl)-3H-indeno[1,2-c]pyridazin-3-one, mp 275.5°–277° C.

EXAMPLE 10

2,4,4a,5-Tetrahydro-7-(1H-benzimidazol-1-yl)-3H-indeno[1,2-c]pyridazin-3-one, mp 272°–274° C.

EXAMPLE 11

2,4,4a,5-Tetrahydro-7-(1H-1,2,4-triazol-1-yl)-3H-indeno[1,2-c]pyridazin-3-one, mp 302°–304° C.

EXAMPLE 12

2,4,4a,5-Tetrahydro-7-(4-thiomorpholiny-3H-indeno[1,2-c]pyridazin-3-one, mp 265°–268° C.

EXAMPLE 13

2,4,4a,5-Tetrahydro-7-[4-(2-pyridyl)-1-piperazinyl]-3H-indeno[1,2-c]pyridazin-3-one, mp 286°–288° C.

The compounds of Examples 14–17 were prepared by using the preparative method of Example 2 by reacting 5-fluoro-2-3-dihydro-1-oxo-1H-indene-2-acetic acid with the appropriate amine substrate in each case. The amine substrate compounds in each example were obtained from commercial sources.

EXAMPLE 14

2,4,4a,5-Tetrahydro-7-(1-morpholinyl)-3H-indeno[1,2-c][1,2-c]pyridazin-3-one, mp 256°–258° C.

EXAMPLE 15

2,4,4a,5-Tetrahydro-7-[(3-aminopropyl)amino]-3H-indeno[1,2-c][1,2-c]pyridazin-3-one monohydrochloride, mp 288°–290° C.

EXAMPLE 16

2,4,4a,5-Tetrahydro-7-(4-methyl-1-piperazinyl)-3H-indeno[1,2-c][1,2-c]pyridazin-3-one, mp 244°–246° C.

EXAMPLE 17

2,4,4a,5-Tetrahydro-7-(butylamino)-3H-indeno[1,2-c][1,2-c]pyridazin-3-one, mp 230°–234° C.

We claim:

1. A compound of the formula

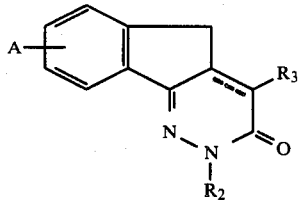

wherein represents a single or double bond; $R_2$ and $R_3$ are independently hydrogen or lower alkyl; and A is selected from

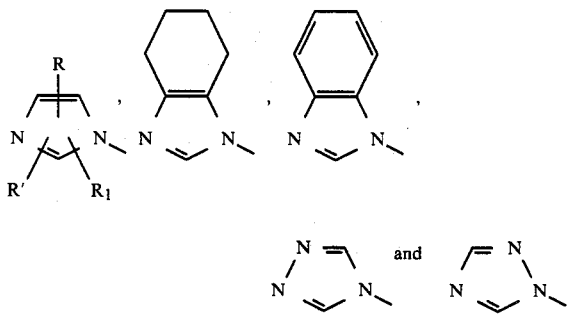

wherein R, R', and $R_1$ are independently hydrogen, lower alkyl, hydroxy lower alkyl; and $R_4$ is hydrogen, halogen, hydroxy, lower alkyl, or lower alkyloxy; wherein lower alkyl has from one to six carbon atoms; and the pharmaceutically acceptable salts thereof.

2. A compound according to claim 1 and being 2,4,4a,5-tetrahydro-7-(1H-imidazol-1-yl)-3H-indeno[1,2-c]pyridazin-3-one, and the pharmacetically acceptable acid addition salts thereof.

3. A compound as claimed in claim 1 and being 2,5-dihydro-7-(1H-imidazol-1-yl)-3H-indeno[1,2-c]pyridazin-3-one, and the pharmaceutically acceptable acid addition salts thereof.

4. A compound as claimed in claim 1 and being 2,4,4a,5-tetrahydro-7-(2-methyl-1H-imidazol-1-yl-3H-indeno[1,2-c]pyridazin-3-one, and the pharmaceutically acceptable acid addition salts thereof.

5. A compound as claimed in claim 1 and being 2,4,4a,5-tetrahydro-7-(2-ethyl-4-methyl-1H-imidazol-1-yl-3H-indeno[1,2-c]pyridazin-3-one, and the pharmaceutically acceptable acid addition salts thereof.

6. A compound as claimed in claim 1 and being 2,4,4a,5-tetrahydro-7-(4-methyl-1H-imidazol-1-yl-3H-indeno[1,2-c]pyridazin-3-one, and the pharmaceutically acceptable acid addition salts thereof.

7. A compound as claimed in claim 1 and being 2,4,4a,5-tetrahydro-7-(4-hydroxymethyl-1H-imidazol-1-yl-3H-indeno[1,2,-c]pyridazin-3-one, and the pharmaceutically acceptable acid addition salts thereof.

8. A compound as claimed in claim 1 and being 2,4,4a,5-tetrahydro-7-(4-phenyl-1H-imidazol-1-yl-3H-indeno[1,2-c]pyridazin-3-one, and the pharmaceutically acceptable acid addition salts thereof.

9. A compound as claimed in claim 1 and being 2,4,4a,5-tetrahydro-7-(4,5,6,7-tetrahydro-1H-benzimidazol-1-yl)-3H-indeno[1,2-c]pyridazin-3-one, and the pharmaceutically acceptable acid addition salts thereof.

10. A compound as claimed in claim 1 and being 2,4,4a,5-tetrahydro-7-(1H-benzimidazol-1-yl)-3H-indeno[1,2-c]pyridazin-3-one, and the pharmaceutically acceptable acid addition salts thereof.

11. A compound as claimed in claim 1 and being 2,4,4a,5-tetrahydro-7-(1H-1,2,4-triazol-1-yl)-3H-indeno[1,2,-c]pyridazin-3-one, and the pharmaceutically acceptable acid addition salts thereof.

12. A pharmaceutical composition for increasing cardiac contractility or for lowering blood pressure comprising an effective amount of a compound as claimed in claim 1 and a pharmaceutically acceptable carrier.

13. A method for increasing cardiac contractility and lowering blood pressure in a patient which comprises administering an effective amount of a pharmaceutical composition according to claim 12.

* * * * *

UNITED STATES PATENT AND TRADEMARK OFFICE
CERTIFICATE OF CORRECTION

PATENT NO. : 4,602,019

DATED : July 22, 1986

INVENTOR(S) : Ila Sircar, James A. Bristol

It is certified that error appears in the above-identified patent and that said Letters Patent is hereby corrected as shown below:

Column 9, Claim 1, line 32, after "wherein" insert -- ----- --.

Signed and Sealed this

Seventh Day of October, 1986

[SEAL]

Attest:

DONALD J. QUIGG

Attesting Officer

Commissioner of Patents and Trademarks